United States Patent [19]

Edwards

[11] Patent Number: 4,515,904

[45] Date of Patent: May 7, 1985

[54] CATALYSTS FOR THE PRODUCTION OF MALEIC ANHYDRIDE BY THE OXIDATION OF BUTANE

[75] Inventor: Robert C. Edwards, Naperville, Ill.

[73] Assignee: Standard Oil Company (Indiana), Chicago, Ill.

[21] Appl. No.: 537,983

[22] Filed: Sep. 30, 1983

[51] Int. Cl.$^3$ .................... B01J 27/14; C07D 307/60
[52] U.S. Cl. .................... 502/209; 502/210; 502/211; 502/212; 502/213; 549/260
[58] Field of Search ............... 502/162, 209, 211, 210, 502/212, 213

[56] References Cited

U.S. PATENT DOCUMENTS

| | | | |
|---|---|---|---|
| 3,293,268 | 12/1966 | Bergman et al. | 502/209 |
| 3,832,359 | 8/1974 | Freerksi et al. | 502/209 X |
| 3,867,411 | 2/1975 | Roffelson et al. | 502/209 X |
| 3,888,886 | 6/1975 | Young et al. | 502/209 X |
| 3,985,775 | 10/1976 | Harrison | 502/209 X |
| 4,092,269 | 5/1978 | Mount et al. | 502/209 |
| 4,132,670 | 1/1979 | Katsumoto et al. | 502/209 |
| 4,147,661 | 4/1979 | Higgins et al. | 502/209 |
| 4,149,992 | 4/1979 | Mount et al. | 502/209 |
| 4,151,116 | 4/1979 | McDermott | 502/204 |
| 4,154,703 | 5/1979 | Umenua et al. | 502/209 |
| 4,222,945 | 9/1980 | Higgins et al. | 502/209 |
| 4,283,288 | 8/1981 | Udovich et al. | 502/209 |
| 4,328,126 | 5/1982 | Udovich et al. | 502/209 |
| 4,337,174 | 6/1982 | Mount et al. | 502/209 |
| 4,361,501 | 11/1982 | Blum et al. | 502/209 |
| 4,392,986 | 7/1983 | Yong et al. | 502/209 |

OTHER PUBLICATIONS

Hackbs Chemical Dictionary 1944 p. 650.

Primary Examiner—William G. Wright
Attorney, Agent, or Firm—Gunar J. Blumberg; William T. McClain; William H. Magidson

[57] ABSTRACT

A process for the manufacture of a phosphorus-vanadium and phosphorus-vanadium-co-metal catalysts suitable for use in the manufacture of maleic anhydride from butane which process comprises reacting at a temperature of about 0° C. to about 200° C. a vanadium compound in an organic ether solvent having about 2 to about 10 carbon atoms with a phosphoryl halide in the presence of water or an aliphatic alcohol having from about 1 to about 8 carbon atoms, eliminating the solvent and activating the catalyst by the addition of butane or other hydrocarbon feedstock and a phosphorus compound at a temperature of about 300° C. to about 500° C. The catalysts are useful for the manufacture of maleic anhydride from butane feedstock.

36 Claims, No Drawings

CATALYSTS FOR THE PRODUCTION OF MALEIC ANHYDRIDE BY THE OXIDATION OF BUTANE

BACKGROUND OF THE INVENTION

1. Field of the Invention

The field of this invention relates to processes for the manufacture of phosphorus-vanadium, and phosphorus-vanadium-co-metal catalysts suitable for the oxidation of butane to maleic anhydride.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well-known, and until recently the principal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,403,943; 4,154,703 and British Application No. 2,019,839A. While the aforementioned prior art tends to bring about some improvement in the performance of the phosphorus-vanadium catalyst there remains much room for improvement, particularly from the standpoint of high conversion, yield, and catalyst life. Other references of interest include U.S. Pat. Nos. 4,020,174; 4,094,816; 4,089,807; 3,296,282; 3,474,041 and British Pat. No. 1,464,198. All these references relate to catalyst reactivation and not to new catalyst preparation.

The object of the present invention is to provide a process for the manufacture of phosphorus-vanadium, and phosphorus-vanadium-co-metal oxide catalysts by carrying out the reaction in an organic solvent using phosphoryl halides as a source of phosphorus and activating the catalysts with phosphoryl halides or alkyl esters of phosphoric acid or other phosphorus containing moieties. A further object is to provide a process for the manufacture of maleic anhydride in the presence of the catalyst manufactured by the novel process.

Our catalyst is suitably prepared in organic solvents by slurrying vanadium compounds and metals or metal oxides such as molybdenum oxide, zinc oxide, uranium oxide, tungsten oxide, tin oxide, bismuth oxide, titanium oxide, chromium oxide, zirconium oxide, niobium oxide, atimony oxides and cobalt oxide in organic solvents, preferably organic ether solvents.

A small amount of water or a hydrogen donor compound, such as a lower alcohol, is also present in the ether. Suitable alcohols are ethanol and methanol and suitable ethers are tetrahydrofuran (THF), tetrahydropyran, 1,2-dimethoxyethane, bis(2-methoxyethyl)ether, 1,4-dioxane, ethylether, propylether, butylether, and pentylether. Phosphoryl halide is slowly added to the slurry. The water or hydrogen donor reacts with the phosphoryl halide to generate anhydrous phosphoric acid and hydrogen halide gas. The hydrogen halide dissolves both the vanadium compound, for example the vanadium pentoxide, and the co-metal compound and also reduces the vanadium from a valence or state of five to a valence or state of four. This reaction takes place at a temperature of about 0° C. to about 200° C.

While the reaction solution is being refluxed, a modifier or mixture of modifiers such as o-xylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid, or trimellitic acid, is suitably added to the reaction solvent. After refluxing, the color of the solution is green. The volume of the solution is reduced by distillation or evaporation until it becomes a thick syrup. This syrup is dried at a temperature of about 120° C. to about 150° C. and 0-15 inches of mercury vacuum under an air purge. Once dry, the color of the solid material is brown. The catalyst can be formed into geometric forms, such as cylinders, using graphite, Sterotex, or other lubricants such as stearic acid, zinc stearate, and starch and binders such as polyvinyl alcohol. The catalyst in the form of geometric shapes or in powder form is suitably calcined in air or a nitrogen-air combination before loading into a suitable tubular reactor. The catalyst is activated further by the addition of phosphorus compounds or mixtures thereof such as alkylphosphates, phosphites, and phosphines. This activation takes place at a temperature of about 300° C. to about 500° C. Representative phosphorus compounds have the following structure:

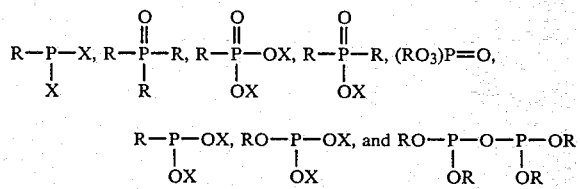

wherein R is phenyl or an alkyl radical of one to 6 carbon atoms and X is H or R. Suitable compounds are primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO_3)P=O$ wherein R is hydrogen or $C_1-C_4$ alkyl, at least one R being $C_1-C_4$ alkyl. The preferred phosphorus compounds are triethylphosphate or trimethylphosphate.

Our catalyst has a much higher yield of maleic anhydride from butane feedstock than catalysts of the prior art, such as those disclosed in U.S. Pat. No. 3,862,146, and U.S. Pat. No. 4,328,126. Among the many advantages of our novel process for the manufacture of the catalyst can be cited the quantitative use of the expensive vanadium and the use of phosphoryl halide as a source of phosphorus and inexpensive solvents such as organic ethers in combination with small amounts of water or methanol or ethanol.

The novel catalyst comprises a phosphorus-vanadium mixed oxide or a phosphorus-vanadium mixed oxide promoted by metals. The atomic ratio of the vanadium to phosphorus can suitably be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, zirconium, niobium, chromium or cobalt to vanadium should be in the range of 0.001:1 to 0.2:1. The atomic ratio of phosphorus to vanadium is suitably in the range of 0.8:1 to 2:1, preferably 1:1 to 1.3:1.

The co-metal, such as molybdenum, zinc, tungsten, uranium, bismuth, titanium, zirconium, antimony, niobium, cobalt, chromium, or tin may be added as a compound together with vanadium, or separately introduced into the solution. Suitable co-metal compounds comprise their oxides and soluble salts. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice, or silica. The catalyst may be reinforced with such materials at any stage in its preparation.

According to our process, the average valence of vanadium is in the range of about 3.8 to 4.2. In our catalyst preparation various phosphoryl halides may be used, but $POCl_3$ is preferred. The catalyst can be activated with:

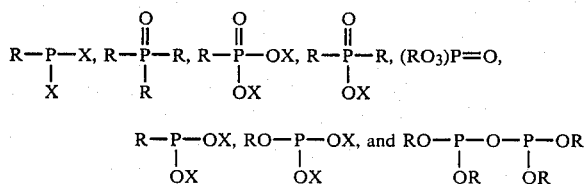

wherein R is phenyl or an alkyl radical of one to 6 carbon atoms and X is H or R. Suitable compounds are the primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO_3)P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO_3)P=O$ wherein R is hydrogen or $C_1-C_4$ alkyl, at least one R being $C_1-C_4$ alkyl. The preferred phosphate compounds are triethylphosphate or trimethylphosphate.

The vanadium compound can be vanadium pentoxide, vanadium tetrachloride, vanadium trichloride, vanadium oxydichloride, vanadium oxytrichloride, vanadium tetraoxide, vanadium oxalate, and most soluble vanadium complexes. Suitable vanadium compounds include: vanadium oxides, such as vanadium pentoxide, vanadium trioxide and the like; vanadium oxyhalides, such as vanadyl chloride, vanadyl dichloride, vanadyl trichloride, vanadyl bromide, vanadyl dibromide, vanadyl tribromide and the like; vanadium containing acids, such as meta-vanadic acid, pyrovanadic acid and the like; vanadium salts, such as ammonium meta-vanadate, vanadium sulfate, vanadium phosphate, vanadyl formate, vanadyl oxalate and the like; however, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic manufactures of oxygen and diluent gases, such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour, and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 25° C. A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite potassium nitrate eutectic constant temperature mixture. An additional method of temperature control is to use a metal block reactor whereby the metal surrounding the tube acts as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes, such as vycor and the like. Both carbon steel and nickel tubes have excellent long life under the conditions of the reaction described herein. Normally, the reactors contain a preheat zone under an inert material such as one-quarter inch alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, super-atmospheric, or below atmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well-known to those skilled in the art. For example, the recovery may be by direct condensation or by absorption in suitable media, with specific operations and purification of the maleic anhydride. The following examples will serve to provide full understanding of the invention, but it is to be understood that these examples are given for illustrative purposes only and will not be interpreted as limiting the invention in any way. In the examples the terms "conversion", "selectivity" and "yield" are defined as follows:

$$\text{Conversion \%} = \frac{\text{Moles n-butane reacted}}{\text{Moles n-butane in feed}} \times 100$$

$$\text{Selectivity \%} = \frac{\text{Moles maleic anhydride produced}}{\text{Moles n-butane feed consumed}} \times 100$$

$$\text{Yield Wt. \%} = (\text{Conversion}) \times (\text{Selectivity}) \times 169$$

EXAMPLE 1

To a 3-liter, 3-neck, round-bottom flask equipped with a thermowell, electrical mantle, mechanical stirrer, and reflux condenser, were added 91 g of $V_2O_5$, 4.4 g of $MoO_3$, 196.3 g of $POCl_3$, and 500 ml of tetrahydrofuran (THF). Water, 69 g, was slowly added from a dropping funnel to the slurry causing the $V_2O_5$ to dissolve and the solvent to reflux. The red-brown solution was refluxed at 103° C. for 13.5 hours reducing the vanadium (V) to vanadium (IV) and turning the color green.

The solvent was distilled from the green solution until a thick syrup remained. The syrup was put in a vacuum oven overnight at 10 in. of Hg vacuum and 130° C. with a slight air purge passing through the oven. The dry catalyst precursor which was brown in color was ground and formed into 3/16" cylindrical tablets using 5 wt. % graphite as a lubricant. The side crush strength of the tablets was 6.5–7.5 lbs.

A 6 cm$^3$ charge of the tablets was loaded into a 0.62" diameter minireactor and evaluated with a feed of 1.1% n-butane in synthetic air at 1200 VHSV. This catalyst gave a maximum maleic anhydride yield of 103 wt. % at a temperature of 741° F. after 53 days on stream. The conversion was 89 mole % and the selectivity 69 mole %. The surface area of this catalyst was 40 m$^2$/g and the pore volume by adsorption was 0.215 cc/g.

EXAMPLE 2

A catalyst precursor was prepared in a similar manner as described in Example 1 except that the solution was refluxed for 11.5 hours. The dried powder was ground, mixed with 5 wt. % graphite, and formed into 3/16" cylinders having a 6.5–8.0 lb. side crush strength. These tablets were calcined to 700° F. in air before being charged into a minireactor and evaluated as reported in Example 1. This catalyst gave a maximum maleic anhydride yield of 102 wt. % at 745° F. The conversion was 90 mole % and the selectivity 67 mole %.

EXAMPLE 3

A catalyst precursor was prepared as reported in Example 1 except that the solution was refluxed for only 5 hours and 184 g of $POCl_3$ were used giving a 1.2/1 P/V ratio instead of 1.28/1 as used in Examples 1 and 2. The powder was mixed with 5 wt. % graphite and formed into 3/16" cylinders having a 6–7 lb. side crush strength.

The catalyst was evaluated in a minireactor as described in Example 1. The catalyst gave a maximum maleic anhydride yield of 100 wt. % at 753° F. with an 89 mole % conversion and a 66 mole % selectivity.

EXAMPLE 4

A catalyst precursor was prepared in a similar manner as in Example 1. Phthalic anhydride, 22 g, was added to the solution which was refluxed for 12.5 hours. The powder was mixed with 5 wt. % graphite and formed into 3/16" cylindrical tablets having a 6–7.5 lb. side crush strength.

The catalyst was evaluated in a minireactor as described in Example 1. A maximum maleic anhydride yield of 100 wt. % was obtained at 741° F. The conversion was 85 mole % and the selectivity 70 mole %. The catalyst surface area was 42 m$^2$/g and the pore volume by adsorption was 0.2787 cc/g.

EXAMPLE 5

A 12-liter, 3-neck, round-bottom flask equipped with an electrical mantle, mechanical stirrer, thermowell, and reflux condenser, was charged with 2 liters of THF, 364 g of $V_2O_5$, 17.6 g of $MoO_3$, and 767 g of $POCl_3$. Water, 270 g, was added slowly causing the $V_2O_5$ to dissolve and turning the solution red-brown. The solution was refluxed for 14.5 hours with the color changing from red-brown to green. Solvent was removed by distillation until the temperature reached 129° C. The thick syrup was put into a vacuum oven at 3–5 in. Hg vacuum and 130° C. with a slight air purge passing through the oven. The dry material was ground, mixed with 5 wt. % graphite, and formed into 3/16" cylindrical tablets having a 5-15 lb. side crush strength. The tablets were calcined in air to 371° C.

This catalyst, 120 g, was loaded into a pilot plant having a 0.62" diameter reactor. After 1219 hours on stream, the catalyst gave a maximum maleic anhydride yield of 77 wt. % at 1.5% n-butane in air feed, 2000 VHSV, and 707° F. salt bath temperature. The feed stream was then passed through a saturator containing a solution of 0.4 g triethylphosphate per liter of water. The catalyst gave a maximum maleic anhydride yield of 87 wt. % at the same conditions and a salt bath temperature of 725° F. after 1723 hours on stream. Thus, the addition of triethylphosphate in small quantities to the feed stream resulted in improving the catalyst yield by 10 wt. %. The concentration of the saturator solution was increased to 0.7 g triethylphosphate per liter of water. After 2395 hours on stream, the yield of maleic anhydride was 89 wt. % at the same conditions and a salt bath temperature of 722° F.

EXAMPLE 6

Using the same experiment set up as described in Example 5, 2 liters of THF, 364 g of $V_2O_5$, 17.3 g of $MoO_3$, and 270 g of water were changed to the large flask. $POCl_3$, 767 g, was added slowly to the mixture causing the $V_2O_5$ to dissolve and turning the color of the solution red-brown. At this time 500 ml of o-xylene were added to the solution and it was refluxed for 16.5 hours causing the solution color to change to green. The solvent was then removed by distillation until the temperature of the catalyst syrup reached 139° C. The syrup was placed into a vacuum oven overnight at 150° C. and 5 in. of Hg vacuum with a slight air purge passing through the oven. The dry brown material was ground, mixed with 5 wt.% graphite, and formed into 3/16" cylindrical tablets having a 3 lb. side crush strength.

A 6 $cm^3$ charge of the tablets was evaluated in a minireactor as described in Example 1. This catalyst gave a maximum matric anhydride yield of 101 wt.% at 778° F. after 22 days on stream. The conversion was 90 mole % and the selectivity was 66.5 mole %.

This example illustrates that an excellent catalyst can be prepared by adding $POCl_3$ to the reaction mixture which contains a hydrogen donor compound. This method of addition gives better temperature control of the exothermic reaction also, the use of the modifier o-xylene, a higher distillation temperature, and a longer reflux time are demonstrated in this example.

EXAMPLE 7

Using the experiment set up described in example 1, 91 g of $V_2O_5$, 4.3 g of $MoO_3$, 184 g of $POCl_3$, and 50 ml of THF were changed to the reaction flask. Water, 65 g, was slowly added in 1 hour to the flask causing the vanadium to dissolve and form a red-brown solution. O-xylene, 150 ml, was added to the reaction solution and it was refluxed for 20.5 hours. Solvent was removed by distillation until the temperature of the catalyst syrup reached 151° C. The syrup was dried overnight in a vacuum oven at 140° C. at 0 in. of Hg vacuum with an air purge passing through the oven.

The dried material was ground, mixed with 5 wt.% graphite, and formed into 3/16" cylinders having a 3 lb. side crush strength. The catalyst was evaluated as described in example 1. The catalyst having a P/V ratio of 1.2/1 gave a maximum maleic anhydride yield of 100 wt.% at 727° F. after 42 days on stream.

EXAMPLE 8

A catalyst was prepared and evaluated as reported in Example 7 except that 11.8 g of zinc metal was used in the catalyst preparation instead of $MoO_3$. This catalyst gave a maximum maleic anhydride yield of 86 wt.% at 822° F. after 50 days on stream.

EXAMPLE 9

A catalyst was prepared and evaluated was described in Example 7 except that 6.96 g of $WO_3$ instead of $MoO_3$ were used in the preparation and the $POCl_3$ was added to the reaction mixture containing the water. This catalyst gave a maximum maleic anhydride yield of 88 wt.% at 736° F. after 49 days on stream.

EXAMPLE 10

A catalyst was prepared and evaluated as described in Example 9 except that 23.19 g of $WO_3$ was used in the preparation. The catalyst gave a maximum maleic anhydride yield of 83 wt.% at 763° F. after 21 days on stream.

EXAMPLE 11

A catalyst was prepared and evaluated as reported in Example 9 except that Sn metal, 3.56 g, was used in place of $WO_3$. The catalyst gave a maximum maleic anhydride yield of 81 wt.% at 761° F. after 29 days on stream.

EXAMPLE 12

A catalyst was prepared and evaluated as described in Example 9 except that $Co_2O_3$, 2.49 g, was used in place of $WO_3$. The catalyst gave a maximum maleic anhydride yield of 87 wt.% at 759° F. after 30 days on stream.

Examples 9-12 show that phosphorus-vanadium catalysts prepared with co-metals other than molybdenum will give excellent yields of maleic anhydride.

EXAMPLE 13

After the catalyst in Example 9 was on stream for 55 days, the feed gas was passed through a saturator containing a 20 wt.% aqueous solution of triethylphosphate. The yield from this catalyst increased to 92 wt.% at 737° F. 10 days later. This treatment improved the yield of this catalyst by 4 wt.%.

EXAMPLE 14

After 27 days on stream the feed gas to the catalyst in Example 10 was passed through a saturator containing a 1-5 wt.% aqueous solution of triethylphosphate. The yield increased to 97 wt.% at 752° F. 18 days later which is a 14 wt.% improvement in the yield of this catalyst.

EXAMPLE 15

The feed gas to the catalyst in Example 12 was passed through a saturator containing a 1-5 wt.% aqueous solution of triethylphosphate after 31 days on stream. The yield increased to 90 wt.% at 759° F. 7 days later for an improvement in yield of 3 wt.%.

Examples 13-15 illustrate that phosphorus-vanadium catalysts having co-metals other than molybdenum, and prepared according this invention, will give improved yields when treated in situ with phosphorus compounds.

We claim:

1. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl halide in the presence of water or an aliphatic alcohol having from about 1 to about 8 carbon atoms, eliminating the solvent and activating the catalyst by the addition of butane or another hydrocarbon feedstock and a phosphorus compound at a temperature of about 300° C. to about 500° C.

2. The process of claim 1 wherein the vanadium compound is vanadium pentoxide.

3. The process of claim 1 wherein the ether is tetrahydrofuran.

4. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, wherein the phosphorus-vanadium oxide catalyst is dissolved and the dissolved phosphorus-vanadium oxide catalyst is solidified by evaporation or distillation of the organic solvent and activating the catalyst by the addition of butane or another hydrocarbon feedstock and a phosphorus compound at a temperature of about 300° C. to about 500° C.

5. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, eliminating the solvent and activating the catalyst by the addition of butane or another hydrocarbon feedstock and an alkylester of orthophosphoric acid at a temperature of about 300° C. to about 500° C.

6. The process of claim 5 wherein the alkylester of orthophosphoric acid has the following structure:

$$(RO)_3P=O$$

wherein R is hydrogen or $C_1$ to $C_4$ alkyl, at least one R being a $C_1$ to $C_4$ alkyl.

7. The process of claim 6 wherein the alkyester is triethylphosphate.

8. The process of claim 6 wherein the alkylester is trimethylphosphate.

9. A process for the manufacture of a phosphorus-vanadium-co-metal oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl halide in the presence of water or an aliphatic alcohol having from about 1 to about 8 carbon atoms, eliminating the solvent and activating the catalyst by the addition of butane or another hydrocarbon feedstock and a phosphorus compound at a temperature of about 300° C. to about 500° C.

10. The process of claim 9 wherein the vanadium compound is vanadium pentoxide.

11. The process of claim 9 wherein the ether is tetrahydrofuran.

12. A process for the manufacture of a phosphorus-vanadium-co-metal oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium-co-metal oxide catalyst is dissolved and the dissolved phosphorus-vanadium-co-metal oxide catalyst is solidified by evaporation or distillation of the organic solvent and activating the catalyst by the addition of butane or another hydrocarbon feedstock and a phosphorus compound at a temperature of about 300° C. to about 500° C.

13. A process for the manufacture of a phosphorus-vanadium-co-metal oxide catalyst suitable for use in the manufacture of maleic anhydride from butane which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst by the addition of butane or another hydrocarbon feedstock and an alkylester of orthophosphoric acid at a temperature of about 300° C. to about 500° C.

14. The process of claim 13 wherein the alkylester of orthophosphoric acid has the following structure:

$$(RO)_3P=O$$

wherein R is hydrogen or $C_1$ to $C_4$ alkyl, at least one R being a $C_1$ to $C_4$ alkyl.

15. The process of claim 14 wherein the alkyester is triethylphosphate.

16. The process of claim 14 wherein the alkylester is trimethylphosphate.

17. A process for the manufacture of a phosphorus-vanadium-co-molybdenum oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst by the addition of butane or another hydrocarbon feedstock and a phosphorus compound at a temperature of about 300° C. to about 500° C.

18. The process of claim 17 wherein the vanadium compound is vanadium pentoxide.

19. The process of claim 17 wherein the ether is tetrahydrofuran.

20. A process for the manufacture of a phosphorus-vanadium-molybdenum oxide catalyst suitable for use in the manufacture of maleic anhydride from butane which process comprises reacting at a temperature of about 0° C. to about 200° C. a vanadium compound in an organic ether solvent having about 2 to about 10 carbon atoms with an alkylester of orthophosphoric acid in the presence of water or an aliphatic alcohol having from about 1 to about 8 carbon atoms, eliminating the solvent and activating the catalyst by the addition of butane or another hydrocarbon feedstock and an alkyl ester of orthophosphoric acid at a temperature of about 300° C. to about 500° C.

21. The process of claim 20 wherein the alkylester of orthophosphoric acid has the following structure:

(RO)₃P=O wherein R is hydrogen or C₁ to C₄ alkyl, at least one R being a C₁ to C₄ alkyl.

22. The process of claim 21 wherein the alkylester is triethylphosphate.

23. The process of claim 21 wherein the alkylester is trimethylphosphate.

24. A process for the manufacture of a phosphorus-vanadium-zinc oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst by the addition of butane or another hydrocarbon feedstock and a phosphorus compound at a temperature of about 300° C. to about 500° C.

25. The process of claim 24 wherein the vanadium compound is vanadium pentoxide.

26. The process of claim 24 wherein the ether is tetrahydrofuran.

27. A process for the manufacture of a phosphorus-vanadium-zinc catalyst suitable for use in the manufacture of maleic anhydride from butane which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst by the addition of butane or another hydrocarbon feedstock and an alkylester of orthophosphoric acid at a temperature of about 300° C. to about 500° C.

28. The process of claim 27 wherein the alkylester of orthophosphoric acid has the following structure:

(RO)₃P=O wherein R is hydrogen or C₁ to C₄ alkyl, at least one R being a C₁ to C₄ alkyl.

29. The process of claim 27 wherein the alkylester is triethylphosphate.

30. The process of claim 27 wherein the alkylester is trimethylphosphate.

31. A process for the manufacture of a phosphorus-vanadium oxide catalyst suitable for use in the manufacture of maleic anhydride from butane with process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, eliminating the solvent and activating the catalyst at a temperature of about 300° C. to about 500° C. by the addition of butane or another hydrocarbon feedstock and a phosphorus compound selected from the group consisting of:

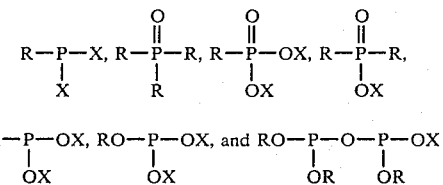

wherein R is phenyl or an alkyl radical of one to 6 carbon atoms and X is H or R.

32. A process for the manufacture of a phosphorus-vanadium-co-metal oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst at a temperature of about 300° C. to about 500° C. by the addition of butane or another hydrocarbon feedstock and a phosphorus compound selected from the group consisting of:

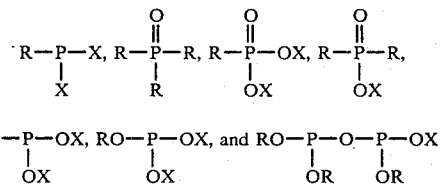

wherein R is phenyl or an alkyl radical of one to 6 carbon atoms and X is H or R.

33. A process for the manufacture of a phosphorus-vanadium-molybdenum oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium-molybdenum oxide catalyst is dissolved and the dissolved phosphorus-vanadium-molybdenum oxide catalyst is solidified by evaporation or distillation of the organic solvent and activating the catalyst by the addition of butane or another hydrocarbon feedstock and a phosphorus compound at a temperature of about 300° C. to about 500° C.

34. A process for the manufacture of a phosphorus-vanadium-molybdenum oxide catalyst suitable for use in the manufacture of maleic anhydride from butane which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst at a temperature of about 300° C. to about 500° C. by the addition of butane or another hydrocarbon feedstock and a phosphorus compound selected from the group consisting of:

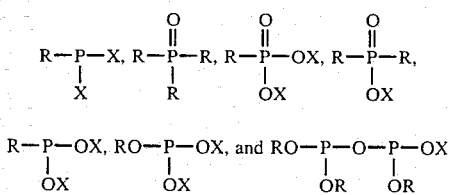

wherein R is phenyl or an alkyl radical of one to 6 carbon atoms and X is H or R.

35. A process for the manufacture of a phosphorus-vanadium-zinc oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium-zinc oxide catalyst is dissolved and the dissolved phosphorus-vanadium-zinc oxide catalyst is solidified by evaporation or distillation of the organic solvent and activating the catalyst by the addition of butane or another hydrocarbon feedstock and a phosphorus compound at a temperature of about 300° C. to about 500° C.

36. A process for the manufacture of a phosphorus-vanadium-zinc oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst at a temperature of about 300° C. to about 500° C. by the addition of butane or another hydrocarbon feedstock and a phosphorus compound selected from the group consisting of:

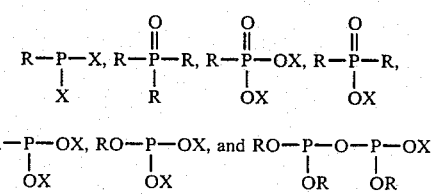

wherein R is phenyl or an alkyl radical of one to 6 carbon atoms and X is H or R.

* * * * *

UNITED STATES PATENT OFFICE
CERTIFICATE OF CORRECTION

Patent No. 4,515,904            Dated  May 7, 1985

Inventor(s)    ROBERT C. EDWARDS

It is certified that error appears in the above-identified patent and that said Letters Patent are hereby corrected as shown below:

Patent

| Column | Line | |
|---|---|---|
| 5 | 32-33 | "super-atmospheric" should be -- superatmospheric -- |
| 8 | 13 | "was" (second occurrence) should be -- as -- |
| 10 | 42 | "alkyester" should be -- alkylester -- |
| 10 | 47 | "vanadium-co-molybdenum" should be -- vanadium-molybdenum -- |

Signed and Sealed this

Fifteenth Day of October 1985

[SEAL]

Attest:

Attesting Officer

DONALD J. QUIGG

Commissioner of Patents and Trademarks—Designate